United States Patent [19]
Takashi

[11] Patent Number: 5,088,314
[45] Date of Patent: Feb. 18, 1992

[54] GAS DETECTING METHOD AND SYSTEM

[75] Inventor: Yamaguchi Takashi, Osaka, Japan

[73] Assignee: Figaro Engineering, Inc., Osaka, Japan

[21] Appl. No.: 354,206

[22] Filed: May 19, 1989

[30] Foreign Application Priority Data

May 19, 1988 [JP] Japan .................................. 63-122734

[51] Int. Cl.$^5$ ...................... G01N 27/04; G01N 27/62
[52] U.S. Cl. .................................. 73/23.21; 73/23.3; 73/23.31; 73/23.34; 73/23.35; 73/31.01; 73/31.02; 73/31.03; 123/489; 128/719; 236/49.3; 422/90; 422/94; 422/95; 422/96
[58] Field of Search .......................... 422/90, 94–96, 422/98; 73/23, 23.21, 31.05, 31.01–31.03, 23.3–23.35; 324/464; 98/2.01; 165/16, 43; 123/489; 128/719; 236/49.3

[56] References Cited

U.S. PATENT DOCUMENTS 4,958,513 9/1990 Yasunaga .............................. 73/23.2

FOREIGN PATENT DOCUMENTS

WO0270 4/1988 PCT Int'l Appl. .

Primary Examiner—David L. Lacey
Assistant Examiner—David Redding
Attorney, Agent, or Firm—Kerkam, Stowell, Kondracki & Clarke

[57] ABSTRACT

A method of and a system for detecting a gas. A histogram of gas sensor outputs in the past is prepared to determine a gas detection threshold value from the histogram. The threshold value is determined, for example, based on the modal sensor output on the histogram. The threshold value is modified based on the width of distribution on the histogram since the width represents the degree of pollution of the background.

4 Claims, 6 Drawing Sheets

GAS DETECTING METHOD AND SYSTEM

FIELD OF THE INVENTION

The present invention relates to detection of gases such as combustible gas, toxic gas, oxygen and water vapor.

TERMINOLOGY

The term "sensor output" as used herein refers to an output which increases when the sensor detects a gas. However, the result can be reverse depending on the type of sensor used.

PRIOR ART

Techniques are known for detecting a gas with use of a gas detection threshold value which is determined based on gas sensor outputs in the past. U.S. Pat. No. 4,437,391 discloses a detection threshold value as determined based on the minimum value of sensor outputs. According to U.S. Pat. No. 4,352,321, the sensor output is sampled at an interval of 1 minute to determine a detection threshold value based on the values obtained. U.S. Pat. application Ser. No. 111,465 discloses that a detection threshold value is to be determined based on the minimum value of gas sensor outputs during a predetermined interval and that the threshold value is to be altered on saturation of the gas sensor output.

The detection threshold value can be determined automatically when gas sensor outputs in the past are used for the determination. This eliminates the need to repeatedly determine the threshold value for a plurality of sensors. If the sensor output varies, for example, with time, the detection threshold value also varies automatically in accordance with the variation and can therefore be made automatically free of the influence of the output variation.

What matters is the meaning of the detection threshold value. Suppose the sensor output increases when the ambient atmosphere is polluted and decreases when it is cleaned. Attention is directed to the minimum output value to determine the detection threshold value using an output reflecting the cleanest atmosphere. The sensor output nevertheless is affected, for example, by temporary cooling of the sensor due to a flow of air, variations in the power supply voltage and variations in the ambient temperature and humidity. Accordingly, the minimum value, if merely used, is likely to afford an unrealistic detection threshold value. Furthermore, a long period of time, when elapsing after the sampling of the minimum value, involves variations in the ambient temperature or humidity or the like, giving rise to a need to alter the detection threshold value. However, the threshold value can not be modified when attention is merely directed to the minimum value only. For example, in the case where the sensor output gradually increases after the minimum value has been sampled, it is impossible to recognize whether the output increase indicates gradual pollution of the atmosphere or a mere increase in the ambient temperature or humidity.

When the detection threshold value is determined by sampling the sensor output every minute, the meaning of the threshold value determined is totally ambiguous. For example, a polluted atmosphere can not be detected with reference to a detection threshold value which is determined from output values of a sensor exposed to this atmosphere. Furthermore, the threshold value fails to reflect the sensor output more than one minute ago.

These problems arise because the detection threshold value is determined from the sensor output at one point instead of utilizing the overall sensor output behavior in the past as a basis for the determination of the value.

SUMMARY OF THE INVENTION

An object of the present invention is to determine a detection threshold value on the basis of the overall sensor output behavior in the past so that the threshold value obtained can be free of the influence of incidental variations in the sensor output.

Another object of the invention is to sample a sensor output for a clean atmosphere from sensor outputs in the past and to determine a detection threshold value based on the values obtained.

Still another object of the invention is to modify the detection threshold value in accordance with the degree of pollution determined of the background itself.

The present invention provides a method of detecting a gas by comparing a gas sensor output with a gas detection threshold value determined based on gas sensor outputs in the past, the method being characterized in that the detection threshold value is determined from a histogram of the gas sensor outputs in the past.

The histogram is converted to the detection threshold value, for example, by using the modal sensor output for the maximum frequency on the histogram, a sensor output corresponding to the median on the histogram, a mean sensor output value determined from the histogram, or the like. The detection threshold value is obtained, for example, by increasing such a value at a suitable ratio.

Preferably, attention is to be directed to the maximum frequency on the histogram. The modal sensor output remains unchanged even if the sensor output varies for an incidental reason. The mode is more preferable than the median or mean. When the sensor is placed in a polluted environment, the median or the mean sensor output value determined from the histogram involves the influence of the pollution. However, the modal sensor output is not appreciably affected by the pollution because the atmosphere is seldom polluted to a definite concentration at all times, such that the histogram has two peaks, i.e., a peak for the clean atmosphere and a peak for the polluted atmosphere. The peak for the polluted atmosphere is broad and concealed by the base of the peak for the clean atmosphere. The detection threshold value, when determined with attention focused on the mode, can therefore be less affected by the pollution of the background.

The width of the histogram corresponds to the degree of changes in the atmosphere. For example, with an environment wherein the background itself is polluted, variations in the background gas concentration give the histogram an increased distribution, which it is desirable to use for modifying the detection threshold value. For example, the threshold value determined from the mode on the histogram is decreased in accordance with the distribution width of the histogram.

The histogram shows the overall sensor output behavior in the past, whereas the mean value or the like of sensor outputs in the past, if used, fails to reflect the data other than the mean value or the like. Furthermore, the memory needed for preparing the histogram can be small and will not greatly burden the control circuit.

The system for practicing the method of the present invention comprises, for example, an A/D converter for subjecting the sensor output to A/D conversion, means for preparing a histogram with use of the converted output, means for determining a detection threshold value from the histogram, and means for comparing the threshold value with a sensor output to detect a gas.

EMBODIMENTS

Figure 1:
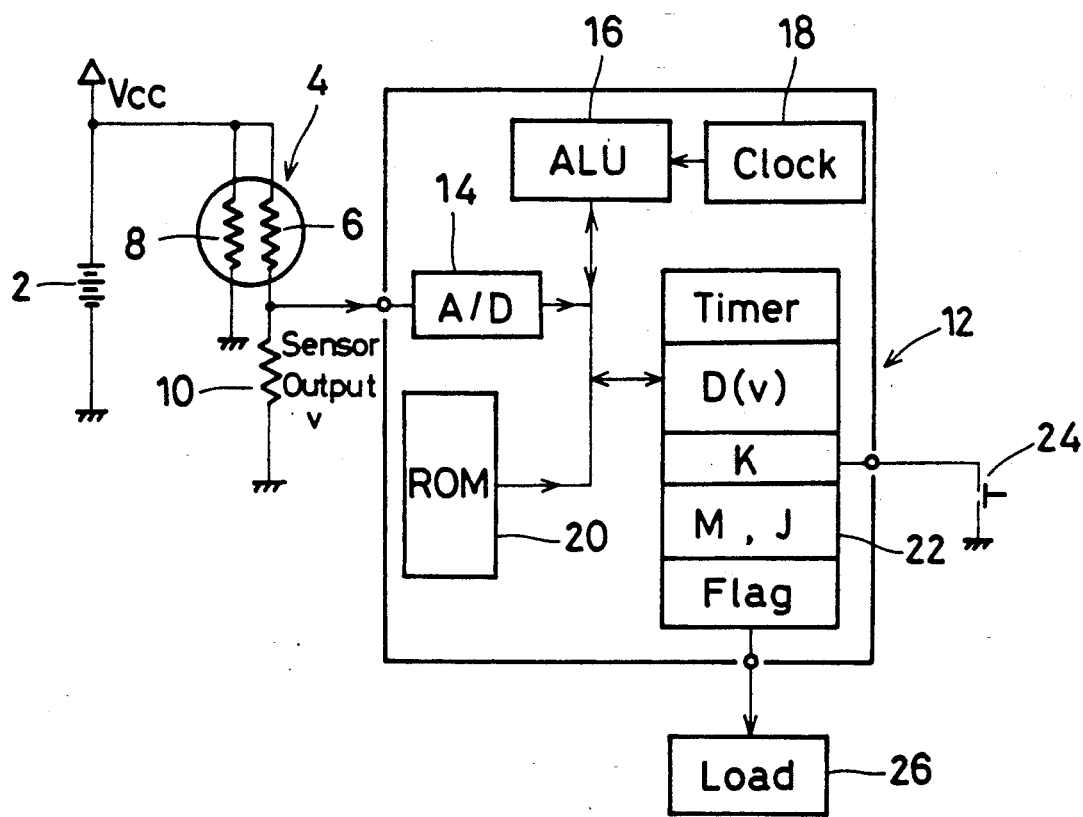
FIG. 1 is a circuit diagram of a first embodiment.
Figure 2:
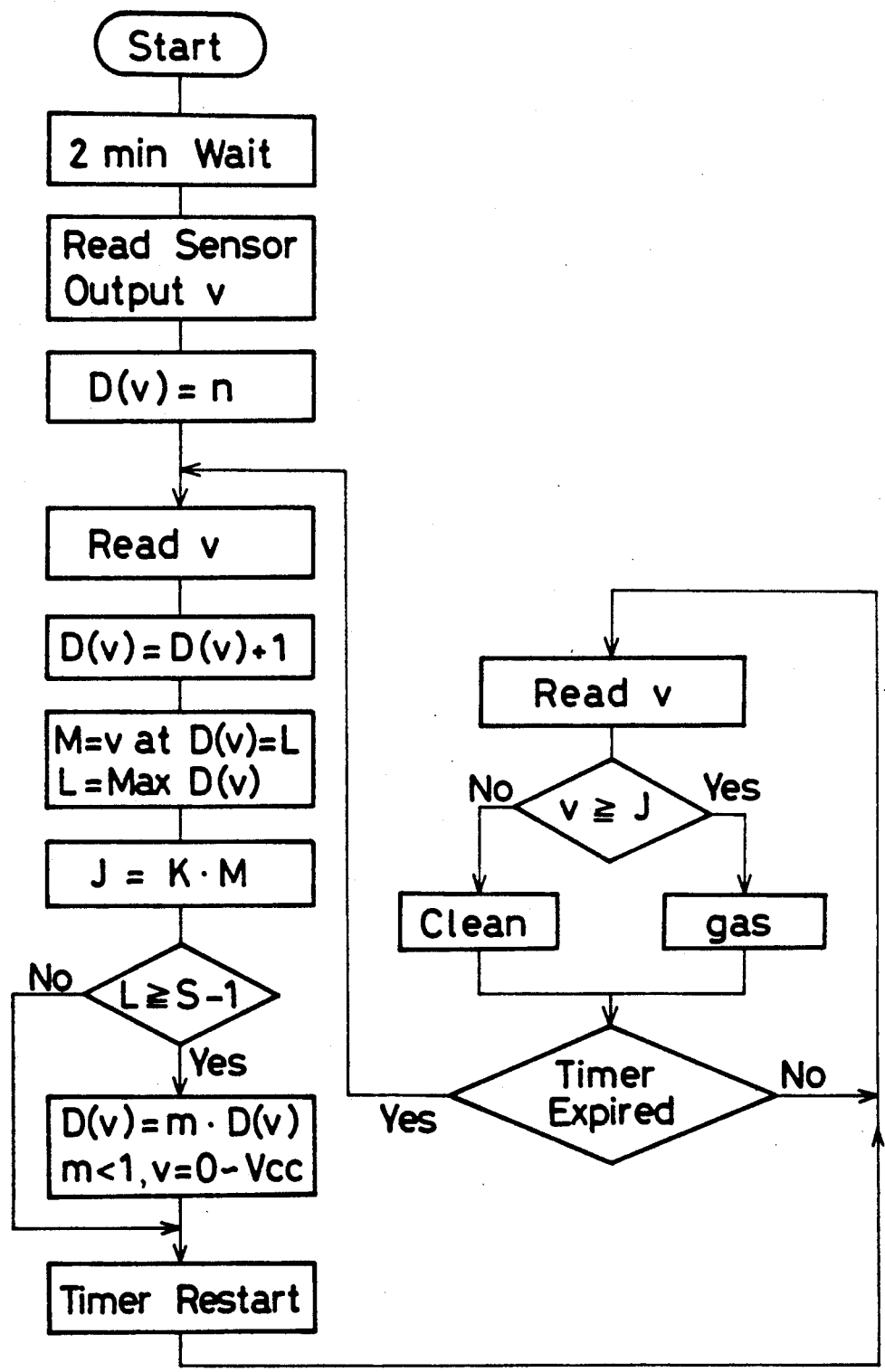
FIG. 2 is a flow chart showing the operation algorism thereof.
Figure 3:
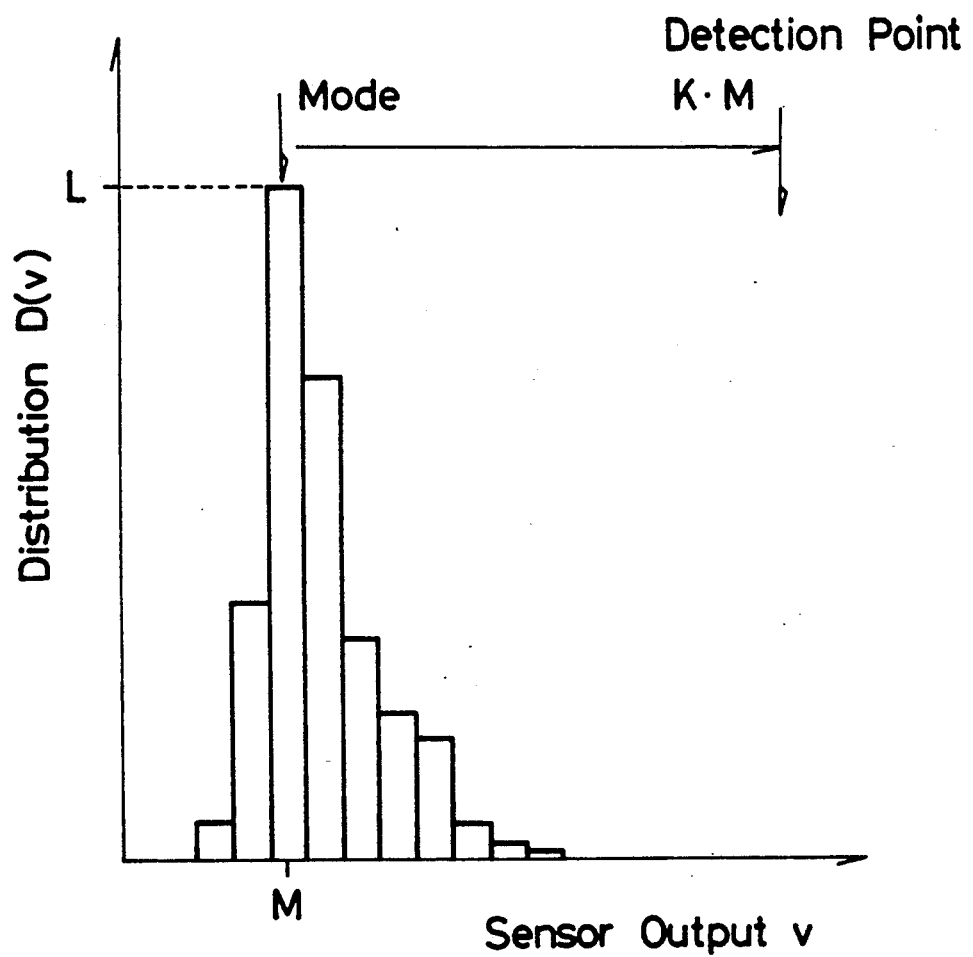
FIG. 3 is a characteristics diagram of the same.

FIGS. 1 to 3 show a first embodiment. With reference to FIG. 1, indicated at 2 is a suitable power supply for giving an output Vcc to the entire system, and at 4 a gas sensor comprising an $SnO_2$ metal-oxide semiconductor 6 and a heater 8 for heating the semiconductor. The resistance value of the metal-oxide semiconductor 6 decreases with an increase in the concentration of a combustible gas, carbon monoxide or like toxic gas, water vapor or the like in the ambient atmosphere. The resistance value of the semiconductor 6 further increases with an increase in the concentration of oxygen, $NO_x$ or ozone in the atmosphere. These gases are detected by the gas sensor 4. Indicated at 10 is a loading resistor for the gas sensor 4, and the voltage v applied thereto serves as the sensor output.

The gas sensor 4 can be optional in its type, material and construction. For example, antimonic acid or like proton conductor may be used for the gas sensor for detecting hydrogen, carbon monoxide, water vapor or the like. The sensor may be of the catalytic combustion type including an oxidizing catalyst for burning a combustible gas by contact therewith and a Pt coil or like temperature measuring resistor for detecting the resulting heat of combustion. In this case, the sensor is used for detecting methane, hydrogen, propane or like combustible gas, or carbon monoxide or like toxic gas. The gas sensor can of course be a $ZrO_2$ or like oxygen sensor, controlled potential electrolytic sensor or the like.

Indicated at 12 is a signal processing microcomputer, at 14 an A/D converter for subjecting the sensor output v to A/D conversion, at 16 an arithmetic and logic unit, at 18 a clock signal generator, and at 20 a ROM having an operation program stored therein. A RAM 22 has a timer for determining a sampling interval for preparing histograms, memory means for storing the values $D(v)$ of the histogram, etc. The histogram shows, for example, sensor output values v as classified at an interval of $\Delta v$ into groups each with a frequency $D(v)$.

The memory required for preparing the histogram is relatively small. Suppose, for example, 100 signals in the past are to be stored. When the signals are classified into 10 groups with frequencies of up to a maximum of 31, the memory required is of $10 \times 5$, i.e., 50 bits. On the other hand, when 100 signals are to be stored directly with signal storage accuracy of 10% $100 \times 3$ (use of 3-bit signals corresponding to 10% accuracy), i.e., 300-bit memory is required.

The RAM 22 also stores the modal sensor output M of the histogram, a detection threshold value J obtained by multiplying the mode M by a constant K, a gas detection signal, etc. The constant K is made variable and can be entered from outside with a switch 24. The modal output M may be converted to the threshold value J by a desired method, for example, by adding a constant to M. The RAM 22 also stores therein flag signals including the gas detection signal. In response to the gas detection signal, an external load 26, such as an air conditioner, gas leak alarm buzzer or the like, is controlled.

With reference to FIG. 2 next, the operation of the system will be described. When the power supply 2 is turned on, a waiting period, e.g. 2 minutes, follows to stabilize the gas sensor 4. At the initial point of time, the histogram is blank, and the values $D(v)$ are all zero. Temporarily, a histogram of initial distribution is prepared by plotting a frequency $D(v)$ of n at a point for the initial sensor output v and a frequency of 0 at the other points. Alternatively, the histogram of initial distribution may be prepared, for example, by plotting the frequency of n for v, a frequency of n/2 on each side thereof, and further a frequency of 3/n for the next adjacent group on each side. Further alternatively, the histogram of initial distribution only may be plotted without conducting any gas detecting operation for a suitable period of time following the energization of the system. A desired initial distribution may be plotted on the histogram.

Next, the current sensor output v is read, and 1 is added to the frequency $D(v)$ corresponding to the value v. The sensor output v for which the frequency is maximum is thereafter taken as a reference value M. Thus, the sensor output v at the maximum frequency $D(v)$ of L is taken as M. The reference value M is multiplied by a constant K to obtain a detection threshold value J. Although the mode is thus used, the median of the distribution or the mean sensor output determined from the distribution may alternatively be used. The histogram can also be so modified that the tail of the histogram at one side thereof where the sensor output is higher is cut off at a suitable position, assuming that a gas is evolved at higher outputs beyond this position. For this purpose, a sensor output is determined from the histogram beyond which the output occurrence frequency is not greater than a predetermined value. The output is used as the detection threshold value. Incidentally, the reference value M may be converted to the detection threshold value J, for example, by adding a predetermined value to M.

The following procedure is taken to avoid the saturation of the memory. It is assumed that the maximum value of frequency $D(v)$ to be stored in the memory is S. The saturation of the memory is precluded by multiplying each frequency value $D(v)$ by m ($m<1$) upon the maximum frequency value L reaching $S-1$. The frequency values need not always be multiplied by the same value m individually but the procedure can be followed, for example, by subtracting a constant from the frequency values $D(v)$.

The histogram can be prepared with the saturation of the memory avoided by the foregoing steps.

For the preparation of the histogram, the sensor output is sampled, for example, at a specified time interval using a timer. More specifically, every time an interval of time set on the timer elapses, the sensor output v is sampled, and the value is plotted on the histogram. The number of sampled values times the sampling interval means a range, in terms of time, of sensor output values in the past which are represented by the histogram. This time range, i.e. period of time, is determined, for example, as follows. For detecting gas leakage, the period is about 1 day to about 3 months. For controlling the introduction of outside air into motor vehicles, the period is about 10 minutes to about 4 hours. For controlling the air conditioners in living rooms, the period is about 30 minutes to about 12 hours. For controlling the interior humidity, it is, for example, about 1 hour to about 48 hours. To detect gas leaks, the histogram is to be prepared over a long period of time and to be modified from season to season so as to obtain a reliable detection threshold value. In controlling the introduction of outside air into motor vehicles, the histogram is to be renewed upon every change in the background atmosphere. For example, there is a difference between the urban area and the suburban area in the concentration of pollutant gases contained in the background. Accordingly, the time to be taken for the preparation of the histogram is s determined that different detection threshold values are used for the urban area and the suburban area during driving. The histogram for use in interior air conditioning is to be prepared over a period of time not exceeding the work time per day.

The current sensor output v is compared with the detection threshold value J, such that the output v, when not smaller than J, is to be interpreted as indicating presence of a gas.

The operation of the system will be described more specifically with reference to FIG. 3. It is now assumed that the system is in use for controlling an air conditioner and that the pollution of the atmosphere is to be detected from the sensor output v, for example, for ventilation. The modal sensor output affords an output corresponding to clean air. Seemingly, the minimum sensor output value corresponds to clean air, whereas the minimum generally reflects a temporary decrease in the sensor output and is irrelevant to the purification of the atmosphere. For example, the sensor output temporarily drops when the sensor 4 is temporarily cooled with a flow of air or when the power source voltage varies. It is then very likely that the reduced output will be sampled as a minimum.

Furthermore, the following needs to be considered. In the case where the ambient atmosphere is polluted, the concentration of the gas pollutant is rarely constant. When a histogram of the sensor output is plotted over a long period of time, a histogram for clean air is obtained as superposed on a histogram for polluted atmosphere. The histogram for the polluted atmosphere has a large width and is not noticeably affected by the maximum frequency on the histogram, whereas the mean or median of sensor output values is altered by the pollution of the ambient atmosphere. Accordingly, with attention directed to the maximum frequency, it is possible to sample the sensor output corresponding to an atmosphere closest to a clean atmosphere. Thus, the sensor output for the clean atmosphere is sampled as the reference value M, from which the detection threshold value J is determined. The current sensor output is compared with the threshold value J to detect the pollution of the atmosphere and drive the load 26 such as a ventilation fan.

Next, detection of gas leakage will be considered. With gas leakage alarms, the sensor output responsive to a leak of gas is measured before the alarm is delivered from the factory, and the alarm is so adjusted as to indicate leakage when the sensor output exceeds the measured value. However this adjusting procedure requires considerable skill. Further unless the sensor 4 is used under an appropriate condition or if the sensor 4 deteriorates with time, the alarm will not operate reliably, as in the case where the alarm is not adjusted properly. Even in such a case, the sensor output responsive to clean air nevertheless differs greatly from the output responsive to a gas leak. Accordingly the sensor output value for clean air is sampled from the histogram to prepare a fail-safe output with the influence of deterioration or the like compensated for.

The sensor output increases owing to a cause, such as use of an organic solvent, irrelevant to gas leakage. An output corresponding to clean air can be sampled free of the influence of such an incidental increase in the output if the histogram is prepared, for example, over a period of about 1 day to about 3 months. With attention directed to the maximum frequency on the histogram, an output more accurately corresponding to clean air can be sampled. The sensor output is likely to markedly decrease temporarily, for example, owing to a decrease in the ambient temperature or humidity, whereas the influence of the incidental decrease in the sensor output can be offset if the histogram is prepared over a long period of time.

Humidity control can be effected, primarily using the detection threshold value determined from the histogram with use of the modal output or the like, for humidity feedback control.

Figure 4:
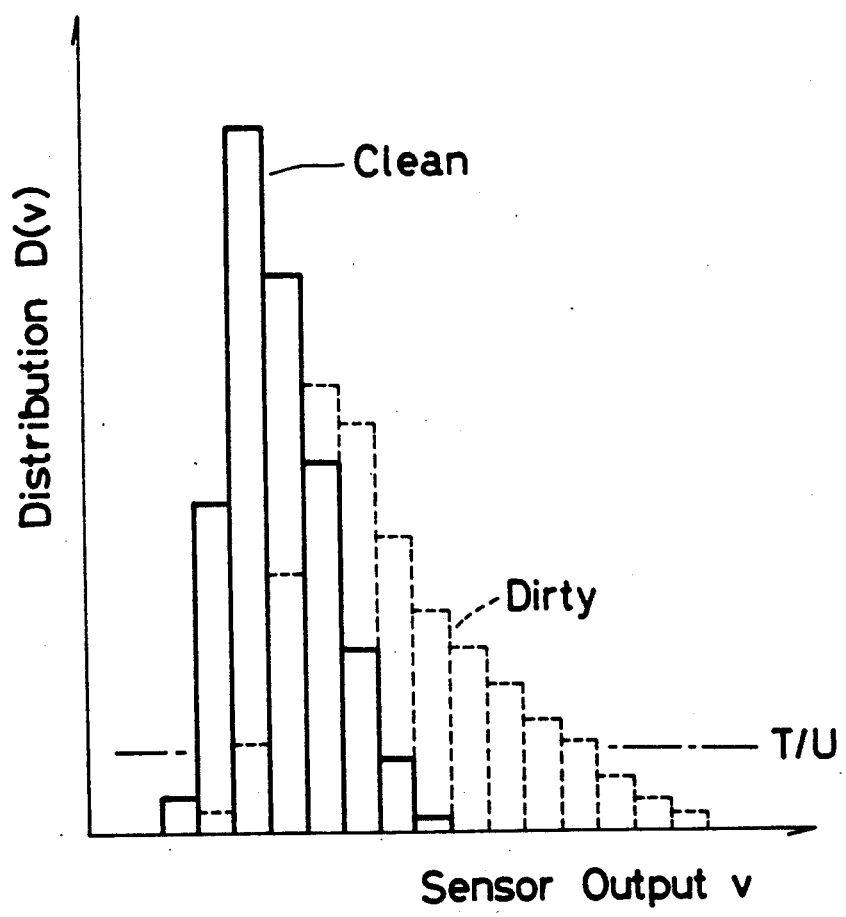
FIG. 4 is a characteristics diagram of a second embodiment.
Figure 5:
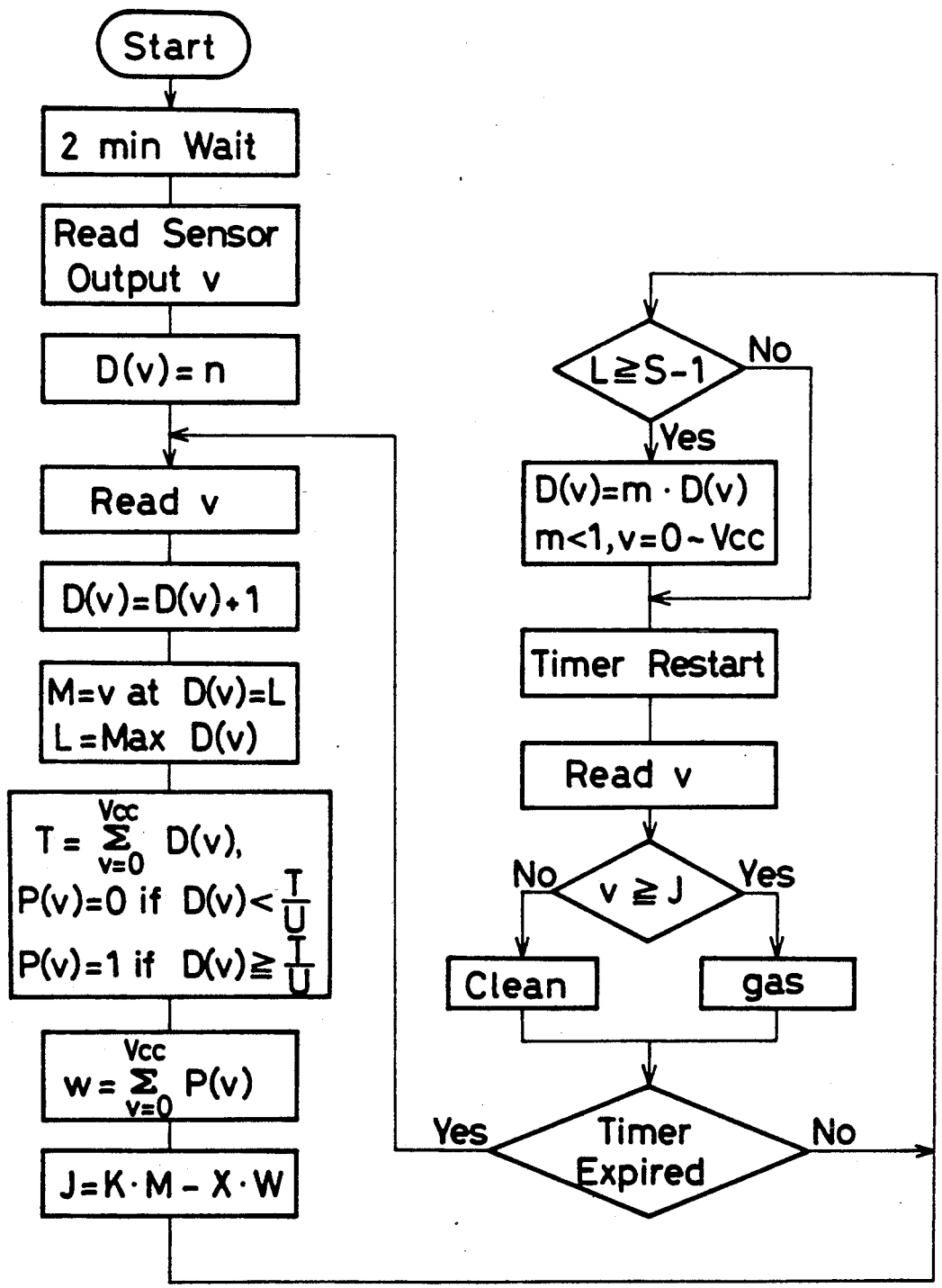
FIG. 5 is a flow chart showing the operation algorism of the same.

FIGS. 4 and 5 show a second embodiment wherein the detection threshold value is modified with use of the distribution width of a histogram. With reference to FIG. 4, a histogram of sensor output for a clean atmosphere is shown in solid lines, and a histogram of sensor output for a polluted atmosphere in broken lines. These histograms are schematic. The feature of the polluted atmosphere is that the histogram has an increased distribution width because the atmosphere is rarely polluted to a constant concentration at all times and because the variations in the concentration of pollutant spread as a wider distribution on the histogram.

Accordingly, a more accurate detection threshold value can be obtained by modifying the threshold value determined from the modal output or the like, using the distribution width of the histogram. FIG. 5 shows an operation algorism so adapted. The total number of output values, T, on the histogram is calculated, 1 is taken as $P(v)$ when the frequency $D(v)$ is not smaller than $T/U$ (U is constant), and 0 is taken for $P(v)$ when the frequency is less than $T/U$. The sum w of the values $P(v)$ approximately corresponds to the distribution width of the histogram. Accordingly, the sum w times a constant of X is subtracted from the value $K \cdot M$ (wherein M is the mode) to obtain a detection threshold value J. In this way, the increase in the threshold value due to the background pollution can be compensated for.

Figure 6:
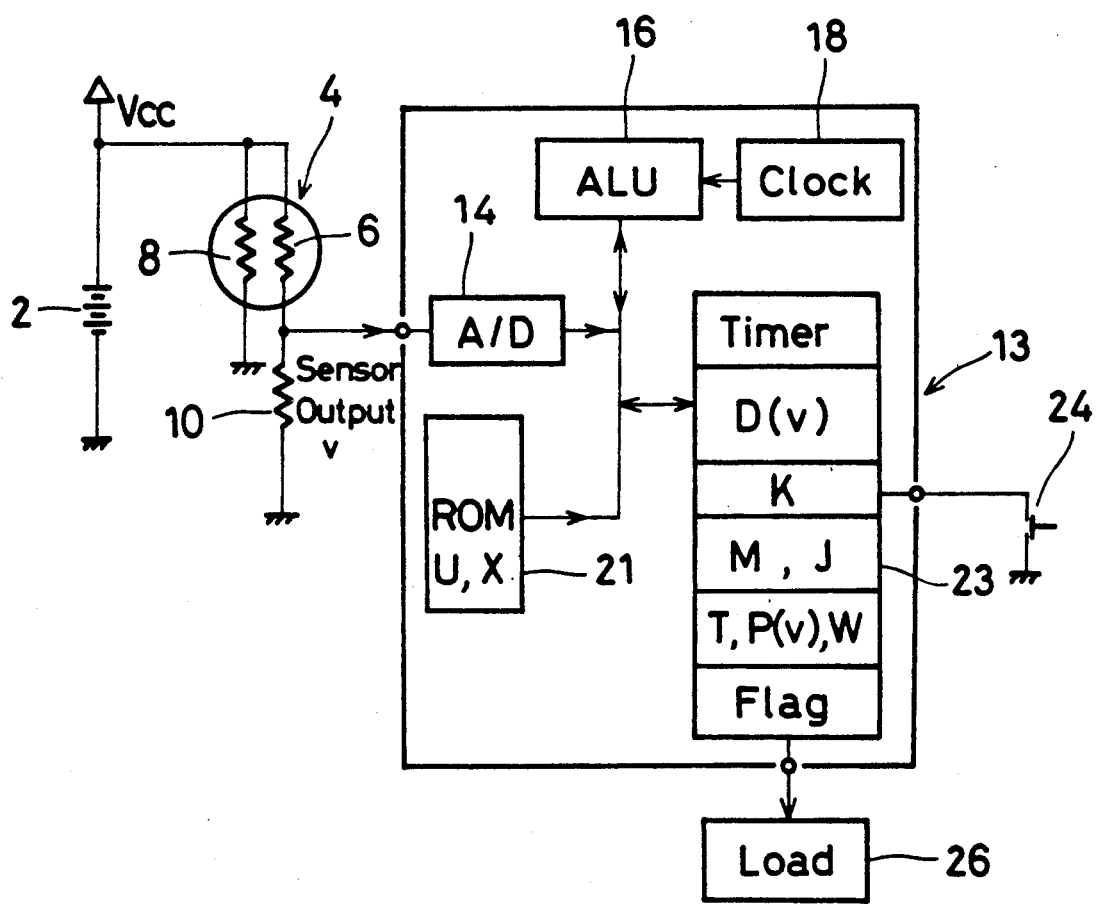
FIG. 6 is a circuit diagram of the same.

FIG. 6 shows a circuit diagram of the second embodiment. The circuit is substantially the same as the one shown in FIG. 1 except that a different microcomputer 13 is used which comprises a ROM 21 having the constants U and X stored therein, and a RAM 23 for storing the variable T, P(v) and W.

We claim:
1. A method of detecting a gas comprising:

preparing a histogram of prior gas sensor detection outputs;

determining a detection threshold value using said histogram; and comparing a gas sensor detection output of said gas with said gas detection threshold value to determine the presence of said gas.

2. A method as defined in claim 1 wherein said detection threshold value is determined based on a modal gas sensor detection output on the histogram.

3. A method as defined in claim 1 wherein said detection threshold value is determined from the gas sensor detection output on at least one point on said histogram and the width of distribution of values (v) for prior gas sensor detection outputs on the histogram.

4. A system for detecting a gas comprising:

a gas sensor;

means coupled to said gas sensor for performing and A/D conversion of a detection output of said gas sensor;

means operatively coupled to said A/D conversion means for preparing a histogram of gas sensor detection output from a plurality of said converted gas sensor detection outputs;

means operatively coupled to said histogram preparing means for determining and storing a detection threshold value based on said histogram; and means operatively coupled to said A/D conversion means and said threshold value storing means for comparing said stored detection threshold value with said converted gas sensor detection output to detect said gas.

* * * * *

UNITED STATES PATENT AND TRADEMARK OFFICE
CERTIFICATE OF CORRECTION

PATENT NO. : 5,088,314
DATED : February 18, 1992
INVENTOR(S) : Takashi YAMAGUCHI It is certified that error appears in the above-identified patent and that said Letters Patent is hereby corrected as shown below:

On the title page item (19)

should be identified as -- Yamaguchi --.

On the title page item [75] Inventor, patentee's name should be -- Takashi Yamaguchi --.

In column 8, line 3 of claim 4: delete "and" and insert -- an --.

Signed and Sealed this

Fourth Day of May, 1993

Attest:

MICHAEL K. KIRK

Attesting Officer

Acting Commissioner of Patents and Trademarks